United States Patent [19]

Veech

[11] Patent Number: 5,629,045
[45] Date of Patent: May 13, 1997

[54] BIODEGRADABLE NOSIOGENIC AGENTS FOR CONTROL OF NON-VERTEBRATE PESTS

[75] Inventor: Richard L. Veech, 712 Brent Rd., Rockville, Md. 20850

[73] Assignee: Richard L. Veech, Rockville, Md.

[21] Appl. No.: 133,753

[22] Filed: Oct. 7, 1993

Related U.S. Application Data

[63] Continuation of Ser. No. 945,887, Sep. 17, 1992, abandoned.

[51] Int. Cl.$^6$ .............. B05D 7/06; A01N 31/00; A01N 33/00; A01N 43/00
[52] U.S. Cl. .............. 427/297; 106/15.05; 106/18.32; 106/18.35; 252/384; 424/78.09; 427/440; 514/277; 514/338; 514/455; 514/511; 514/646; 514/656; 514/678; 514/691; 514/741; 523/122; 523/177
[58] Field of Search .............. 106/15.05, 18.32, 106/18.35; 252/384; 426/425, 429, 430, 650, 651, 655; 424/78.09; 514/277, 338, 455, 511, 646, 656, 691, 678, 741; 427/297, 440; 523/122, 177

[56] References Cited

U.S. PATENT DOCUMENTS

| | | | |
|---|---|---|---|
| 4,012,531 | 3/1977 | Viani | 426/542 |
| 4,158,708 | 6/1979 | Chiovani et al. | 426/651 |
| 4,198,432 | 4/1980 | Vitzthum et al. | 426/650 |
| 4,400,398 | 8/1983 | Coenen et al. | 426/430 |
| 4,774,080 | 9/1988 | Yamamori et al. | 523/122 |
| 4,788,302 | 11/1988 | Costlow et al. | 106/15.05 |
| 4,939,149 | 7/1990 | Blumberg | 514/691 |
| 4,985,265 | 1/1991 | Duboc et al. | 426/655 |
| 5,094,782 | 3/1992 | Chen et al. | 514/691 |
| 5,143,545 | 9/1992 | Stiffey et al. | 106/15.05 |
| 5,226,380 | 7/1993 | Fischer | 114/222 |
| 5,397,385 | 3/1995 | Watts | 106/18.32 |
| 5,441,743 | 8/1995 | McGinnis et al. | 424/407 |

FOREIGN PATENT DOCUMENTS 55-105601  8/1980  Japan .

OTHER PUBLICATIONS

Chemical Abstracts No. 97:194550 (1992) no month.
Chemical Abstracts No. 99:119574 (1983) no month.
Chemical Abstract No. 101:52201 (1984) no month.
Chemical Abstracts No. 110:97221 (1988) no month.
Chemical Abstracts No. 117:66940 (1992) no month.
Chemical Abstract No. 123:115611 (1995) no month.

*Primary Examiner*—Anthony Green
*Attorney, Agent, or Firm*—Hill, Steadman & Simpson

[57] ABSTRACT

Fouling of marine structures such as boats by shell bearing sea animals which attach themselves to such structures, such as barnacles, is inhibited by coatings containing lipid soluble, non-toxic, biodegradable substances which prevent the animals from sitting down on the structures. These substances attack the nervous system of the barnacle, neutralize the glue extruded by the barnacle, and otherwise prevent the barnacles from attaching themselves to surfaces immersed in the aqueous marine environment while being benign to the environment. A preferred inhibitor is pepper containing capsaicin. The inhibitor is incorporated into standard marine paints, impregnants, varnishes and the like.

13 Claims, No Drawings

BIODEGRADABLE NOSIOGENIC AGENTS FOR CONTROL OF NON-VERTEBRATE PESTS

This is a continuation, of application Ser. No. 07/945, 887, filed Sept. 17, 1992, now abandoned.

BACKGROUND OF THE INVENTION

1. Field of the Invention

This invention relates to the art of keeping marine structures such as boats' pilings, bunkers, foundations, land implanted wood structures and the like free from barnacles, clams, oysters, mussels and like shell forming sea life forms from diverse, phyla including annelida, mollusca, arthropoda, insecta and rhodophyta which attach themselves or bore into such structures, without polluting the environment; and wooden structures on terrestrial environment subject to damage from boring pests such as termites, carpenter ants, wood bores and the like, and specifically deals with inhibiting materials for such structures which will not release long-lived toxic pollutants to the surrounding environment.

2. Description of the Prior Art

Heretofore fouling of marine structures by shell forming marine animals, such as above noted, and hereinafter generally termed barnacles, has been somewhat inhibited by toxic substances which pollute the aqueous environment. These toxic substances are not biodegradable and have become a major source of pollution and damage to aquatic life.

One type of barnacle inhibiting treatment has been the painting of the marine structures with a soft paint which continuously flakes off and thus provides an unstable surface receiving the barnacle. This type of treatment requires frequent painting and pollutes the aqueous environment with paint flakes. The treatment is only applicable for low speed boats adapted to be removed from the water and repainted at least once a year. The treatment is not suitable for most boats or other marine objects such as permanently immersed docks or bunkers. Thus, if the flaking paints are applied to the bottoms of relatively high speed fishing boats, pleasure boats, and the like, substantially all of the bottom paint is removed after a very few high speed runs. Also, the cost of annual painting of slow speed boats, such as tankers is prohibitive. Obviously, once the barnacle encrusted paint flakes off, the underlying structure such as the uncoated hull of a boat is a haven for barnacle encrustation.

Another known treatment for decreasing barnacle encrustation on marine structures has been the incorporation of generalized toxins in the paint such as heavy metal compositions such as tributyl tin, tributylamines, tributyl phosphate, arsenicals, and the like. These materials are toxic and not biodegradable. They pollute the surrounding environment to such an extent that aquatic life perishes and valuable oyster beds are soon destroyed.

It would thus be an improvement in this art to inhibit barnacle and the like encrustations on marine structures with long-lasting protective coatings containing non-toxic, biodegradable inhibitors which prevent the barnacles or the like from attaching themselves to the structures. These inhibitors are either repugnant to the barnacle itself or can destroy or neutralize its glue substance so as to stop the barnacle in the act of sitting down on the coating. The exposure of the non-toxic, biodegradable repellant is benign to the surrounding aqueous environment and the aquatic life therein.

SUMMARY OF THE INVENTION

According to this invention, biochemical lipid soluble substances having limited release rates to an aqueous environment and so incompatible with, or repugnant to, sea animals which attach themselves to structures immersed in the aqueous environment as to inhibit attachment to the structures, are incorporated into long lasting coatings or impregnating compositions in amounts which will not reduce the useful life of the coating or repellant and will remain benign to the environment. These substances stimulate, by neurogenic mechanisms, an aversive response which discourages the barnacle from sitting down on the structure to which it seeks attachment. In nature, the free swimming barnacle selects a place to adhere and then excretes a "super glue" to form a permanent bond with the surface during the act of sitting down on this surface. Once attachment has occurred, the bond between the surface and the shell of the barnacle is so strong that it can only be removed by very forceful abrasion which can damage the surface.

The young barnacle goes through a free swimming larval state before attaching itself to the surface and the treatment of this invention inhibits the "sitting down" state of the barnacle and the excretion of the "super glue" for attaching the barnacle to the receiving surface.

My efforts to provide a paint combating barnacles in a manner which avoids the use of a non-biodegradable generalized toxins such as organic tins, included an analysis of the biochemical mechanisms of special importance to the barnacle in its adhesion process; and identification of lipid soluble compounds suitable for admixture with paint which have a limited release rate into aqueous environment, and which are subject to biodegradation by the normal mechanisms, meaning in general these compounds are biochemicals, as opposed to products of organic synthesis and are economically available natural products.

Upon identification of such products they may be added to paint either singly or in combination or even used alone. Because mutations to resistant species is probable in the barnacle, several different agents acting on different biochemical mechanisms may be added to antibarnacle paint at one time. The principle of multiple drug therapy is conspicuously successful in the treatment of MOPS in Hodgkin's Disease and in the poly drug treatment of tuberculosis. The same biochemical principles may here be applied to the inhibition of barnacle growth.

A central factor is inhibition of the "sitting down" reaction of the barnacle, which requires neural control mechanisms, as the barnacle swims in a free environment and selects a place to adhere. This is mediated via the nervous system and involves sensory receptors of the proprioceptive type carried in unmyelinated C-fibers which are found in this species and many other diverse lower phyla. The inhibition of the nervous control required in this process is important to effective barnacle inhibition.

It was generally believed that mammals of this type were only effective in vertebrates. I have shown that arthropods, mollusks and other lower organism compounds stimulating the capsaicin receptor activates aversive response. It is the interference with these receptors and possibly other receptors in cells which form my basic attack via paint or coating preparations.

The "super glue" extruded by the barnacle contains ethyl or isobutyl 2-cyanoacrylate, which is polymerized to form the glue and is neutralized by the lipid soluble, biodegradable antibarnacle substances used in the paint.

I have found that the growth of barnacles on the bottom of a boat located in the Chesapeake Bay was inhibited fourfold by the admixture of small amounts of ground cayenne pepper to a conventional marine paint. I believe the capsaicin in this pepper acts to prevent the barnacle or other similar creatures from sitting down on a surface.

Capsaicin is available from a large number of plants of the Capsicum genus, family Solanaceae, including *Capsicum frutescens.* Common names for this material are paprika, cayenne pepper, tabasco pepper, and the like. All produce a "hot" taste in man and contain the same active principal from the major component capsaicin such as nordehydrocapsaicin, dehydrocapsaicin, homocapsaicin and homodihydrocapsaicin. The structure of the active principal isolated from paprika or cayenne was of molecular weight 305.4, comprised of $C_{18}H_{27}NO_2$ and named N-[(4-hydroxy-3 methoxphenyl) methyl)]-8methyl-6-nonenamide.

The material can be solvent extracted from the dried plant with organic solvents such as petroleum ether, alcohol, ethyl acetate, acetone or super critical fluids such as $CO_2$. It is practically insoluble in cold water and will have a long life when exposed to conventional aqueous environment inhabited by barnacles.

The capsaicin is subject to degradation by a wide variety of enzymatic mechanisms existing in many organisms and therefore it does not constitute any prominent biological hazard to the aqueous environments. The material is available in commercial quantities as a natural plant product.

Any materials which bends to the capsaicin receptor and triggers influx of ions, principally $Ca_{2+}$ and Na, into the cell so as to elicit a nosiogenic response may also be used for barnacle retardation, wood preservation, etc. Other similar chemical materials may be used, including Gingerol, Piperi, Eugenol, Resiniferatoxin or *Leptogorgia virgulata.* These compounds may also be made synthetically with or without modification and/or derivatives. (See diagrams)

SUBSTANCES WHICH ACT ON THE CAPACIN CLASS OF NOCIOCEPTORS

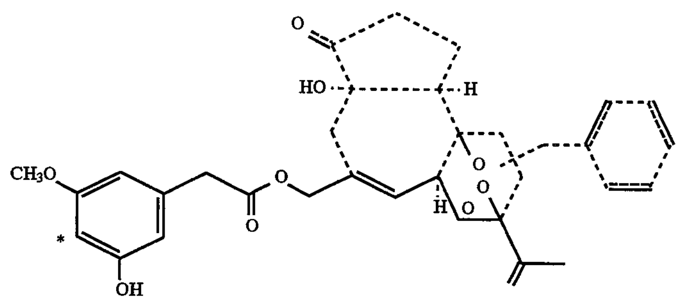

Resiniferatoxin
*m- or p-substitution

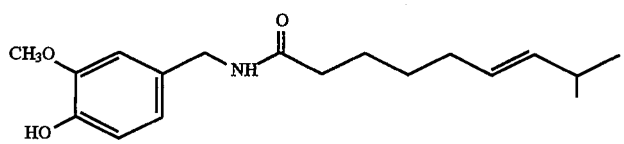

Capsaicin

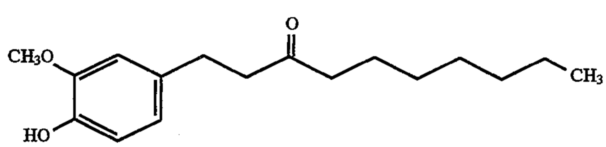

Gingerol

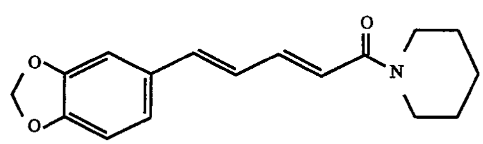

Piperine

CAPSINOIDS (SYNTHETIC DERIVATIVES)

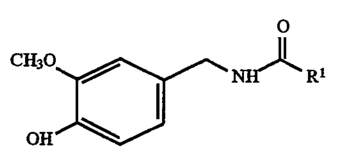

n

Vanilly octanamide 6

Vanilly pelargonamide 7

Vanilly capramide 8

| | |
|---|---|
| Vanilly undecanamide | 9 |
| Vanilly undecenamide | 8 |

Other inhibitors of the "sitting down" action of barnacles are antibiotic calcium ionophores, calimycin, beauvericin, plant terpene forskolin, ecdysone, carbonic anhydrase inhibitors such as acetazolamide and polyamine formation inhibitors such as difloromethylornithine.

Calcium ionophores interfere with the regulation of the normal intracellular level of calcium and adversely affect the "sitting down" or colonization of the barnacle.

Because of the importance of calcium in the life cycle of the barnacle as well as the presence of the calcitonin gene related peptide in the neurons disordering of calcium homeostasis is another major specific target of antibarnacle paints. A number of natural calcium inhibiting products which are lipid soluble are suitable for inclusion in the antibarnacle paint including calimycin, agent A23187. The material is effective on cells at a concentration of $10 \times 10^{-6}M$ and is commercially available.

An alternative calcium ionophoric antibiotic which is also a natural product and is lipid soluble is beauvericin.

Further, the plant terpene forskolin mimics the action of the capsaicin. This material is derived from the roots of *Coleus forskohlii*, a plant terpene of molecular weight 410 which is soluble in ethanol while being essentially insoluble in water. It is an ideal additive to the paint for inhibiting barnacle growth.

Ecdysone, extracted from yew leaves with alcohol or other lipid solvents, is also useful in an antibarnacle paint in that it prevents the accumulation of calcium necessary for the hardening of the newly formed shell of the barnacle after molting. This occurs about every 10 days and since the material is lipid soluble, it will have appreciable lethal qualities to the barnacle.

Formation of a hard shell on the barnacle requires alkalinization above the ambient sea water pH of about 8.05 and this requires carbonic anhydrase which is inhibited by compounds such as acetazolamide. This material is only sparingly soluble in water and would be a suitable additive to the antibarnacle paint.

Since, as explained above, barnacle glue is formed from acrolein, a product of the polyamines, its formation can be blocked by inhibitors of the enzyme ornithine decarboxylase of which a classic example is difloromethylornithine. The material is suitable for addition to the barnacle retardant paint and is biodegradable.

While capsaicin is the preferred antibarnacle agent for incorporation into the paints or other coatings, according to this invention, it will be understood that many other agents repugnant to the barnacles which are benign to the aqueous environment and compatible with conventional marine paint compositions are useful. In general, these substances are lipid soluble, non-toxic, biodegradable, relatively insoluble in sea water, and having the capacity to prevent the barnacle from sitting down on the structure to which it seeks to permanently attach itself.

DESCRIPTION OF BEST MODE EMBODIMENTS OF THE INVENTION

I. Two ounces of commercial cayenne pepper was added to one gallon of commercial tough finish marine bottom paint, stirred in, and applied as conventional. Half of one boat bottom was painted with the pepper containing bottom paint and the other half was painted with the same marine paint, but not containing the pepper.

The commercial paint that was used is known as Wolsey #733 having the following analysis:
1) 42% cuprous oxide
2) 8% titanium oxide
3) 2% phthalocyanian green
4) 20% vinyl resin
5) 11% aromatic hydrocarbons
6) 11% ketone The dry painted hull was immersed in Chesapeake Bay for an entire summer boating season. At the end of the season, the boat was pulled from the water and the barnacles scraped by hand from both sides. The yield of the removed barnacles was weighed. It was found that the weight of barnacles produced on the cayenne pepper painted side was decreased by a factor of four. The cleaned painted surface was grainy and rough to the touch due to the coarseness of the pepper particles.

Another batch of commercial ground cayenne pepper was pulverized in a jet pulverizer to a micron particle size of about 1 –10. This finely ground powder was then incorporated into the same marine paint in the same amount as described above in connection with the use of the commercial sized cayenne pepper granules. When painted and dried on a smooth surface, it was found that the "rough" feeling of the painted surface experienced with the commercial pepper powder was avoided and a smooth painted surface was maintained.

II. This example comprises alternative methods of obtaining the antifouling agent. Whole peppers from the Capsicum genus (species *C. fruitescens L., C. annum L. var coincides Irish, C. annum L. var largum Sandt* and Louisiana sport pepper) are extracted for their constituent capsinoids, capsaicin, homocapsaicin, dihydrocapsaicin, homodihydrocapsaicin and nordihydrocapsaicin. A 90% ethanol, 10% deionized water solution is used in a Soxhlet extraction of the crushed fruit material. The capsaicinoids are then partitioned from the extract solution into petroleum ether and concentrated. Other solvents may be used for extraction and partitioning, including alternative alcohols, methyl chloride, chloroform, linseed oil and ethyl acetate. 10-fold dilutions of the concentrated material (containing 0,027 g/ml. of capsaicin or 0.087) are then prepared, added to marine paint at 0.5, 5, 50% v/v, or used alone, and applied to wooden blocks of uniform dimensions. The blocks are then suspended in the natural saturnine environment of the Chesapeake Bay for a period of 3 months. After this time the colonizing barnacles on each block of wood are removed, and their dry weight determined. Using this dose-response method, the most effective concentration of capsaicinoids with regard to prevention of marina fouling is determined.

The minimal effective dose added to Wolsey bottom paint was 0.0003M final concentration of capsaicin in the paint to achieve a 4-fold decrease in weight of hard fouling at the end of the season. Increasing the concentration of capsaicin by 1000 times had no adverse effects on the quality of the paint and totally inhibited hard fouling by all marine barnacles and tube worms as well as red algae which form calciferous shells.

The addition of an ethyl acetate extract of capsaicin and dihydrocapsaicin as they occur in the dried red pepper powder gave a solution 0.073M (4 gm/180 ml). Making various marine paints 5% (0.0036M in capsaicin) completely inhibited all barnacle growth on the test rod when added to: Wolsey vinylast bottom paint, a vinyl resin polymer; Micron CSC bottom paint, a methylmethacrylate polymer; and Devoe ABC-3 bottom paint. Addition of 10 times this amount to regular Wolsey deck paint, not containing copper, triorthocresyl phosphate or any other commonly used antifouling materials in use also prevented barnacle attachment and growth to test rods.

This demonstrates that the vehicle containing these additives is not critical for their effective action. Nevertheless, the release rate of these materials from paint is an important consideration in the length of time marine coatings would be effective. Accordingly, these material could be added to paint in a manner which prolongs their release. Examples of such addition would be the mixing of extracts of these materials with Bentonite, DuPont hollow nylon fibers, or inclusion in other inert encapsulating agents designed to slow down the release of these materials from paint.

III. This example comprises a method of obtaining active ingredients from purified sources. Capsaicin is extracted from the commercially available powdered drug (1g.) by heating under reflux for 10 minutes with 10 mls. of methylene chloride. The filtrate is added to marine bottom paint and applied as described in example II.

IV. This example illustrates the use of resiniferatoxin as an effective antifouling agent, and a method of extracting the same. Plant parts (fruit, leaves and petioles, stem and roots) from several Euphorbia species (*E. poisionii, E. resinfera* and *E. unispina*) are extracted using the method and bioassay described in example II. Other plant species may be extracted for epoxy-hydrox-derivatives of resiniferonol, for example plants from the genus Mura sp. and Hippomane sp.

V. This example illustrates a method for use of capsaicin and resiniferatoxin as the effective constituents of wood preservative. Capsaicin is extracted from commercial cayenne pepper by heating under reflux with ethanol. The filtrate is impregnated into wood samples of uniform surface area. Impregnation is achieved by total immersion of the wood in the extract solution in a pressure vessel at elevated temperature for several hours. The impregnated strips are then dried, weighed and buried in soil at a depth of approximately 0.25 m. for 3 months. Control strips are subjected to the same process without addition of capsaicin to the impregnation solution. After this time the wood samples are recovered, dried and weighed. Capsaicin is found to significantly reduce loss of mass of the wood material at a concentration of 100 uM impregnation solution.

Wooden tongue depressors, 6 inches by ¾ inch were coated on half of their length with an ethyl acetate extract of crude red pepper powder which was subsequently lyophilized to remove excess solvent until it contained about 0.027 g/ml or 0.087 moles/liter of capsaicin. One ml of this material was painted upon both sides of the tongue depressor for one-half its length. The concentration of capsaicin added was therefore about 87 umoles or 15 umole/sq. inch of surface. The tongue depressor was then buried for 2.5 months near a termite nest. On removal, it was determined that the untreated portion of the tongue depressor had 2 areas which had been eaten away, one in the mid portion, and another right at the edge of the capsaicin treated area. The capsaicin treated wood had no visible evidence of its wood having been eaten.

Dosages of other agents binding to the capsaicin receptor could be decreased in accordance with their binding constants. Thus, resiniferitoxin, which binds to the receptor with about 100 times the affinity of capsaicin, could be used as approximately 100 times less dosages than was used in the above example. Conversely, agents such as eugenol, which have less binding capacity than capsaicin, would require an increased dosage.

Resiniferatoxin may be extracted from Euphorbia sp. as detailed in example 4, and impregnates into wood as described above capsaicin, either as the sole anti-barnacle agent, or in combination with capsaicin.

An alternative method for impregnating wood with capsaicin and resiniferatoxin is to incorporate the extracts with a detergent such as "tween 80" in, for example, a 90% water/10% alcohol solution. The resulting mixture is then applied to the wood under vacuum pressure. This decreases the required impregnation temperature and therefore increases operator safety. These methods avoid the potentially environmentally harmful impregnation processes that utilize ammonia, chromium and arsenic compound mixtures.

VI. This example illustrates the use of capsaicinoids and resininferatoxin as effective mollusc repellents. The feeding and locomotory response of snails was observed: 1) after tactile and chemical stimulation with a capsinoid extract (40 mM) administered to the mantle on the end of a toothpick; and 2) after tactile stimulation only. The capsinoid extract significantly increased the percentage withdrawal response, and was often observed to cause the snail to loose grip and fall from the side of the experimental apparatus. One half of the bottom of a 6-inch diameter petri dish was coated with 0.5 ml of an ethyl acetate extract of red pepper powder containing 40 mM capsaicin and allowed to dry over 48 hours. Water was then placed in the dish and three snails placed in the dish with algae. It was observed that during grazing around the dish, the snails would approach the coated side of the petri dish whereupon they withdrew, then went forward multiple times before turning about in times of 2 to 5 minutes to continue grazing on the uncoated side of the petri dish. Over a period of 3 hours, no snails were observed to occupy the coated side of the dish. This is an example of an aversive response elicited by materials of this class.

From the above descriptions, it will be apparent to those skilled in this art that lipid soluble biodegradable, nontoxic substances attacking the "sitting down" process of barnacles and the like prevent fowling of marine structures treated therewith without polluting the aqueous environment in which these treated structures are immersed.

In accordance with the above description, antibarnacle treatment is designed for inclusion in marine paint primarily used on hull bottoms. It will be noted, however, that where porous hull material, such as wood, is used, the antibarnacle agents may be added to penetrating solutions as well as coatings. In addition, the coating vehicle can be an unpigmented material such as a varnish, epoxy resin, or the like.

I claim as my invention:

1. A method for preserving wood, comprising the steps of:
    extracting capsaicin from commercial cayenne pepper by heating under reflux with ethanol to produce an extract containing a wood preserving amount of capsaicin;
    immersing a wood sample fully in the extract in a pressurized vessel at an elevated temperature for approximately several hours; and thereafter, drying the wood.

2. A method for preserving wood with capsaicin and resiniferatoxin, comprising the steps of:

extracting capsaicin and resiniferatoxin from organic materials to provide extracts containing wood preserving amounts of capsaicin and resiniferatoxin, respectively;

mixing the extracts with a detergent to provide a mixture; and thereafter applying the mixture to a wood sample under vacuum pressure.

3. An antifouling additive comprising a composition containing an antifouling amount of an antifouling agent selected from the group consisting of: resiniferatoxin, gingerol, vanilly octanamide, vanilly pelargonamide, vanilly capramide, vanilly undecanamide, vanilly undecenamide, forskolin and difluoromethylornithine.

4. An antifouling coating composition effective to inhibit attachment of shell-forming organisms on wood and water-immersible structures comprising:

a coating base; and an antifouling amount of an antifouling additive selected from the group consisting of: resiniferatoxin, gingerol, vanilly octanamide, vanilly pelargonamida, vanilly capramide, venilly undecanamide, vanilly undecenamide, forskolin, diluoromethylornithine and mixtures thereof.

5. An antifouling coating composition as defined in claim 4, wherein said coating base is paint.

6. An antifouling coating composition as defined in claim 4, wherein said coating base is marine paint.

7. An antifouling coating composition as defined in claim 4, wherein said coating base is varnish.

8. An antifouling coating composition as defined in claim 4, wherein said coating base is an epoxy resin.

9. An antifouling coating composition as defined in claim 4, wherein said coating base is a penetrating solution.

10. A wood preservative composition comprising:

an organic solvent; and a wood preserving amount of a preservative agent selected from the group consisting of: capsaicin, resiniferatoxin and mixtures of capsaicin and resiniferatoxin.

11. A wood preservative composition as defined in claim 10, further comprising a detergent. thereof.

12. A method of inhibiting attachment of shell-forming organisms on wood and water immersible structures comprising:

applying an antifouling coating composition of a surface of wood or water immersible structure, said antifouling coating composition comprising a coating base and an antifouling amount of an antifoculing additive selected from the group consisting of: resiniferatoxin, gingerol, vanilly octanamide, vanilly pelargonamide, vanilly capramide, vanilly undecanamide, vanilly undecenamide, forskolin, difluoromethylornithine and mixtures thereof.

13. A method for protecting wood from insect pests comprising applying a wood preservative composition to a surface of wood, said wood preservative composition comprising an organic solvent and a wood preserving amount of a preservative agent selected from the group consisting of capsaicin, resiniferatoxin and mixtures of capsaicin and resiniferatoxin.

* * * * *